US009823230B2

(12) United States Patent
Hirata et al.

(10) Patent No.: US 9,823,230 B2
(45) Date of Patent: Nov. 21, 2017

(54) INSULATING GRIP AND APPARATUS FOR A GAS SENSOR

(71) Applicant: NGK INSULATORS, LTD., Nagoya-shi, Aichi (JP)

(72) Inventors: Shodai Hirata, Frankfurt am Main (DE); Koichi Masuda, Nagoya (JP); Kenji Isaka, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 34 days.

(21) Appl. No.: 14/643,397

(22) Filed: Mar. 10, 2015

(65) Prior Publication Data
US 2015/0260698 A1    Sep. 17, 2015

(30) Foreign Application Priority Data

Mar. 12, 2014   (JP) .................................. 2014-048307

(51) Int. Cl.
*G01N 33/00*    (2006.01)
*G01N 15/10*    (2006.01)
(Continued)

(52) U.S. Cl.
CPC ...... *G01N 33/0036* (2013.01); *G01M 15/102* (2013.01); *G01N 27/4078* (2013.01); *G01N 33/0037* (2013.01)

(58) Field of Classification Search
CPC ........... G01N 33/0036; G01N 27/4078; G01N 33/0037; G01M 15/102
(Continued)

(56) References Cited

U.S. PATENT DOCUMENTS 5,679,226 A * 10/1997 Furusaki ............ G01N 27/4062
                                                    204/424
6,241,865 B1 * 6/2001 Cappa .................. G01N 27/407
                                                    204/408
(Continued)

FOREIGN PATENT DOCUMENTS

DE    102012207762 A1    11/2013
JP        53-55564 U       5/1978
(Continued)

OTHER PUBLICATIONS

Translation of JP 2013156183A.*
The Extended European Search Report for the corresponding European patent application No. 15158092.5 dated Aug. 17, 2015.
The Office Action for the corresponding Japanese application No. 2014-048307, issued on Sep. 26, 2017.

*Primary Examiner* — Natalie Huls
*Assistant Examiner* — Monica S Young
(74) *Attorney, Agent, or Firm* — Global IP Counselors, LLP

(57) ABSTRACT

In a gas sensor, not only a tube 70 covers lead wires 48, but also the tube 70 covers an outer peripheral surface of an end portion of an outer cylinder 46 including an open end 46a. A portion of the outer peripheral surface of the outer cylinder 46 covered with the tube 70 is gripped by a clamp 80. Thus, the clamp 80 integrally grips the tube 70 and the outer cylinder 46. Moreover, the tube 70 protrudes from the clamp 80 to a side of the outer cylinder 46 opposite from the open end 46a (protrusion amount L>0). Further, the open end 46a of the outer cylinder 46 forms a large-diameter portion whose outer diameter is larger than an inner diameter D1 of the clamp 80.

8 Claims, 7 Drawing Sheets

(51) Int. Cl.
*G01N 27/407* (2006.01)
*G01M 15/10* (2006.01)

(58) Field of Classification Search
USPC .......................................... 73/23.31
See application file for complete search history.

(56) References Cited

U.S. PATENT DOCUMENTS

| | | | | |
|---|---|---|---|---|
| 6,487,890 B1* | 12/2002 | Weyl | ................. | G01N 27/4077 |
| | | | | 73/23.31 |
| 2001/0054552 A1* | 12/2001 | Matsuo | ................. | G01N 27/407 |
| | | | | 204/421 |
| 2005/0145013 A1* | 7/2005 | Hayashi | ................. | G01N 27/407 |
| | | | | 73/31.05 |
| 2007/0017193 A1* | 1/2007 | Nishio | ................. | B01D 39/1692 |
| | | | | 55/492 |
| 2016/0223504 A1* | 8/2016 | Yonezu | ................. | G01M 15/102 |
| | | | | 73/23.2 |

FOREIGN PATENT DOCUMENTS

| | | |
|---|---|---|
| JP | 11-72462 A | 3/1999 |
| JP | 11-506216 A | 6/1999 |
| JP | 2014-126419 A | 12/2012 |
| JP | 2013-156183 A | 8/2013 |
| JP | 2013156183 A * | 8/2013 |

* cited by examiner

RELATED ART

INSULATING GRIP AND APPARATUS FOR A GAS SENSOR

BACKGROUND OF THE INVENTION

1. Field of the Invention

The present invention relates to a gas sensor.

2. Description of the Related Art

There has hitherto been known a gas sensor that detects the concentration of a predetermined gas, such as $NO_x$, in a measurement target gas, for example, exhaust gas from an automobile. For example, a gas sensor described in PTL 1 includes cylindrical body formed of metal, a detection element (sensor element) disposed within the cylindrical body to detect the gas concentration, and lead wires having electrical continuity to the sensor element and extending outward from the cylindrical body. The gas sensor described in PTL 1 further includes a tube surrounding the lead wires, a cover member, and a clamp member.

FIG. 11 is an explanatory view of an end portion of such a gas sensor 300 of the related art. The gas sensor 300 includes an outer cylinder 346 within which an unillustrated sensor element is disposed, lead wires 348 extending outward (upward in FIG. 11) through an opening at an upper end of the outer cylinder 346, and a tube 370 surrounding the lead wires 348. The gas sensor 300 further includes a cover member 390 that covers an upper side of the outer cylinder and a lower side of the tube 370 from the periphery, and a clamp member 380 that clamps a portion of the cover member 390 covering the upper side of the outer cylinder 346 from the outside. At an upper side of the cover member 390, a contact portion 392 is provided to be in contact with an outer peripheral surface of the tube 370 within the cover member 390. In the gas sensor 300, the existence of the cover member 390 restricts water from entering the sensor from the opening at the upper end of the outer cylinder 346.

CITATION LIST

[PTL 1] Japanese Unexamined Patent Application Publication No. 2013-156183

SUMMARY OF THE INVENTION

However, in such a gas sensor of the related art, the clamp member 380 clamps the cover member 390 and the outer cylinder 346. For this reason, the tube 370 is sometimes insufficiently fixed, for example, the tube 370 comes off the cover member 390 to the upper side in FIG. 11. If the tube 370 comes off the cover member 390, in some cases, the lead wires 348 are exposed or water is likely to enter the sensor.

The present invention has been made to overcome such a problem, and a main object of the invention is to more reliably fix a tube.

A gas sensor according to the present invention includes:
a sensor element;
a cylindrical body in which the sensor element is disposed, the cylindrical body having an open end;
a lead wire having electrical continuity to the sensor element and extending outward from an inside of the cylindrical body through the open end;
a tube that covers an outer peripheral surface of an end portion of the cylindrical body including the open end and a portion of the lead wire extending outward from the open end; and
a grip member that grips a portion of the outer peripheral surface of the cylindrical body covered with the tube so that the tube protrudes to a side opposite from the open end.

In the gas sensor of the present invention, not only the tube covers the lead wire, but also the tube covers the outer peripheral surface of the end portion of the cylindrical body including the open end. The portion of the outer peripheral surface of the cylindrical body covered with the tube is gripped by the grip member. Thus, the grip member integrally grips the tube and the cylindrical body. Moreover, the tube protrudes from the grip member to the side of the cylindrical body opposite from the open end. Consequently, the tube is unlikely to come out from the open end of the cylindrical body, and the tube can be fixed more reliably. Herein, it is only necessary as long as one or more lead wires are provided. For example, the tube may cover a plurality of lead wires.

In the gas sensor of the present invention, the maximum outer diameter of a portion of the tube closer to the open end than the portion gripped by the grip member may be larger than or equal to an inner diameter of the grip member. With this, the grip member is unlikely to come off from the open end of the cylindrical body, and the tube can be fixed more reliably. In this case, the open end of the cylindrical body may serve as a large-diameter portion.

In the gas sensor of the present invention, the grip member may be a ring-shaped member that surrounds the outer peripheral surface of the cylindrical body. This allows the tube to be more reliably fixed by the grip member than, for example, when the grip member is C-shaped such as to surround only a part of the outer peripheral surface of the cylindrical body.

The gas sensor of the present invention may include an elastic body through which the lead wire penetrates, the elastic body being disposed within the cylindrical body to seal the inside of the cylindrical body from an outside of the open end, and the cylindrical body may have a diameter-reduced portion that swages the elastic body from a periphery. In this case, the elastic body can close the gap between an inner peripheral surface of the cylindrical body and the lead wire. This can further restrict water from entering the sensor element from the open end of the cylindrical body.

DETAILED DESCRIPTION OF THE INVENTION

Figure 1:
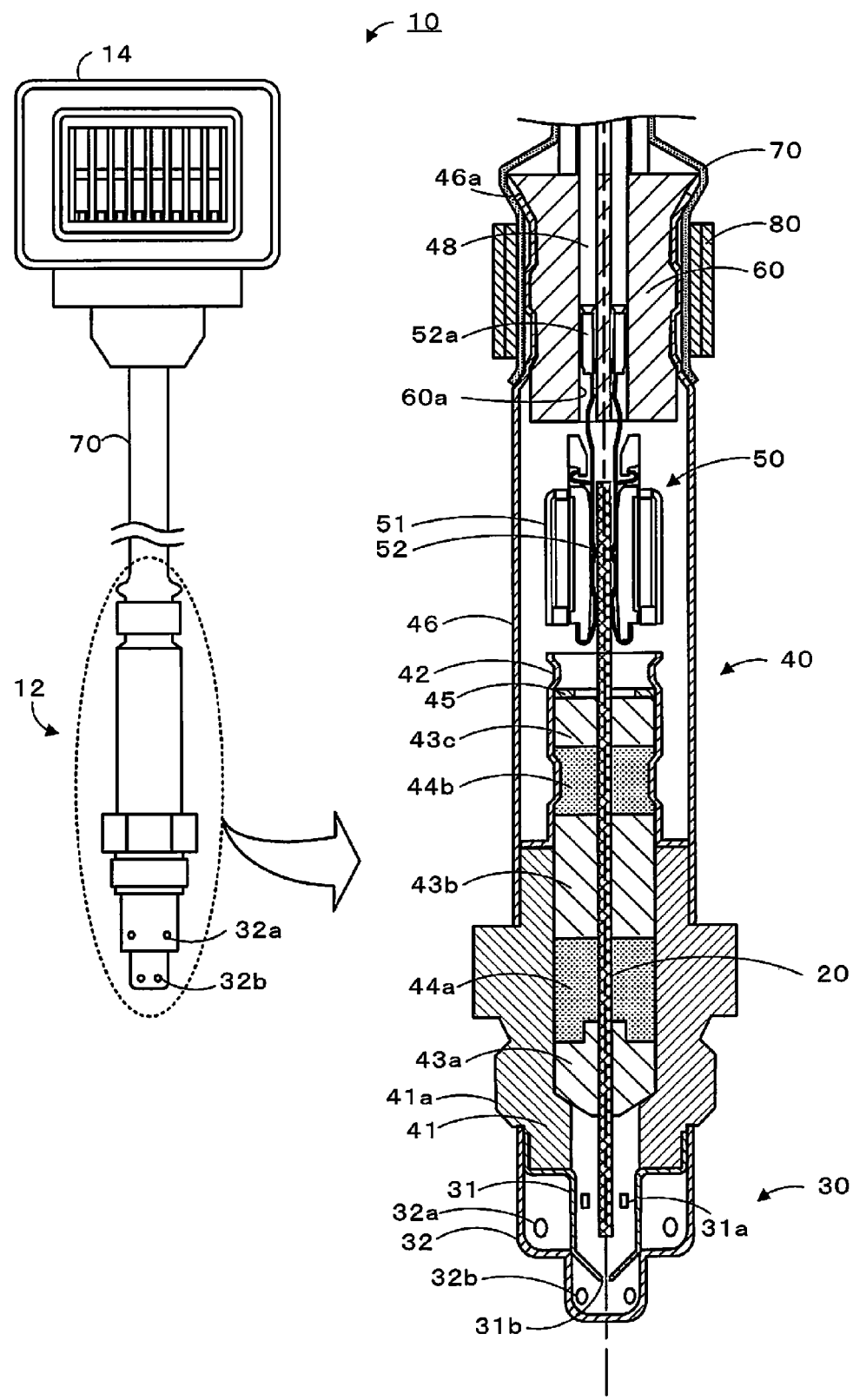
FIG. 1 is a schematic explanatory view illustrating the configuration of a gas sensor 10.

Next, an embodiment of the present invention will be described with reference to the drawings. FIG. 1 is a schematic explanatory view illustrating the configuration of a gas sensor 10 according to an embodiment of the present invention. As illustrated in FIG. 1, the gas sensor 10 includes a sensor body 12, an external connecting part 14, and a tube 70 that covers a plurality of (eight in the embodiment) lead wires 48 for connecting the sensor body 12 and the external connecting part 14. For example, the gas sensor 10 is attached to an exhaust gas pipe in a vehicle, and is used to measure the gas concentration of $NO_x$, $O_2$, or the like contained in an exhaust gas serving as a measurement target gas.

The sensor body 12 includes a sensor element 20 that measures the gas concentration of a predetermined gas component from the measurement target gas, a protective cover 30 that protects one end portion of the sensor element 20, and a sensor assembly 40 including a connector 50 having continuity to the sensor element 20 and a rubber plug 60.

The sensor element 20 is an element shaped like a long and narrow plate, and is formed by, for example, stacking six ceramic substrates formed by oxygen-ion conductive solid electrolyte layers such as zirconia ($ZrO_2$). An end portion of the sensor element 20 on a side of the protective cover 30 (lower end in FIG. 1) is referred to as a free end, and an end portion of the sensor element 20 on a side of the connector 50 (upper end in FIG. 1) is referred to as a base end. On a front surface and a back surface of the base end of the sensor element 20, unillustrated electrodes are provided to apply voltage to the sensor element 20 and to take out electromotive force or current generated in accordance with the concentration of the gas component to be detected by the sensor element 20. A plurality of electrodes are provided on the front surface and the back surface of the sensor element 20, and have continuity to electrodes in the free end of the sensor element 20 via an electrical circuit in the sensor element 20 (not illustrated).

The protective cover 30 is disposed to surround the periphery of the free end of the sensor element 20. The protective cover 30 includes an inner protective cover 31 that covers the free end of the sensor element 20 and an outer protective cover 32 that covers the inner protective cover 31. The inner protective cover 31 is cylindrical, and has inner protective cover holes 31a and 31b through which the measurement target gas ventilates. The outer protective cover 32 is shaped like a bottomed cylinder, and has, in its side surface, outer protective cover holes 32a and 32b through which the measurement target gas ventilates. For example, the inner protective cover 31 and the outer protective cover 32 are formed of metal such as stainless steel.

The sensor assembly 40 includes a main metal piece 41 formed of metal, an inner cylinder 42 and an outer cylinder 46 that are cylindrical and are fixed to the main metal piece 41 by welding, a connector 50 connected to the base end of the sensor element 20, and a rubber plug 60 attached to the outer cylinder 46. The main metal piece 41 can be attached to, for example, an exhaust gas pipe of a vehicle at an external thread portion 41a. Within the main metal piece 41 and the inner cylinder 42, a plurality of ceramic supporters 43a to 43c, and ceramic powders 44a and 44b, such as talc, filled between the ceramic supporters 43a and 43b and between the ceramic supporters 43b and 43c are sealed. These components are sealed while being disposed among a metal ring 45, an inner wall of the main metal piece 41, and an inner wall of the inner cylinder 42. The outer cylinder 46 covers the peripheries of the inner cylinder 42, the sensor element 20, and the connector 50. On an inner side of an end portion of the outer cylinder 46 including an open end 46a (upper end of the outer cylinder 46 in FIG. 1), the rubber plug 60 is attached.

The connector 50 includes a housing 51 formed of a ceramic material such as an alumina sintered body, and contact metal pieces 52 held in the housing 51 to be in contact with the electrodes of the sensor element 20. The contact metal pieces 52 are extended to the outside of the connector 50 and are electrically connected to the lead wires 48 in connecting portions 52a formed by crimped terminals. The lead wires 48 are extended to the outside of the sensor assembly 40. The connector 50 includes a number of (for example, four or eight) of contact metal pieces 52 corresponding to the plural electrodes provided on the front surface and the back surface of the sensor element 20. For this reason, a plurality of (for example, four or eight) connecting portions 52a are provided, and a plurality (for example, four or eight) of lead wires 48 are extended.

The rubber plug 60 is an elastic body that is formed of fluororubber to seal a gap between the outer cylinder 46 and the lead wires 48 (connecting portions 52a) at the open end 46a of the outer cylinder 46. In through holes 60a penetrating the rubber plug 60, the connecting portions 52a are disposed, and the lead wires 48 are extended therethrough. A plurality of through holes 60a are provided to receive the plural connecting portions 52a and the plural lead wires 48.

Figure 2:
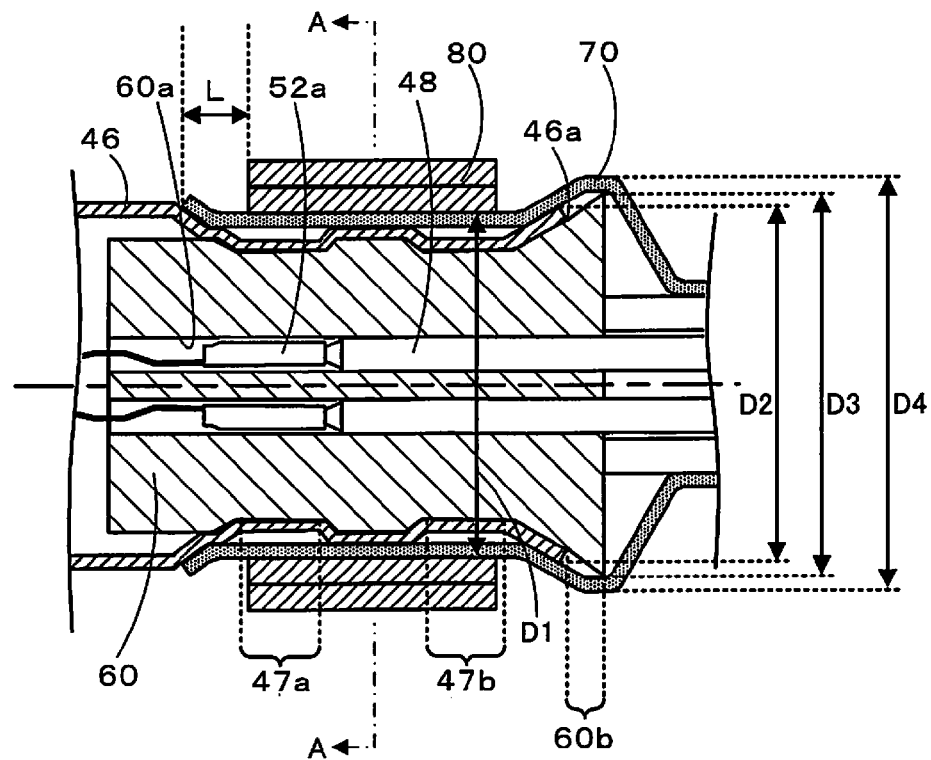
FIG. 2 is an enlarged cross-sectional view of a side (base end side) of an open end 46a of a sensor body 12.

FIG. 2 is an enlarged cross-sectional view of the side of the sensor body 12 at the open end 46a (base end side). As illustrated in the figure, the outer cylinder 46 has swaged portions 47a and 47b swaged in a diameter-reduced form. By the swaged portions 47a and 47b, the rubber plug 60 is swaged in a diameter-reduced form together with the outer cylinder 46, and is fixed within the outer cylinder 46. The rubber plug 60 has a protruding portion 60b protruding outward (toward the right side in FIG. 2) from the open end 46a. This rubber plug seals the inside of the outer cylinder 46 from the outside of the open end 46a, and allows the lead wires to be extended outward from the outer cylinder 46 while restricting, for example, water from entering the outer cylinder 46.

The tube 70 is a cylindrical member having the insulating property and flexibility, and covers the entire lead wires 48 between the sensor body 12 and the external connecting part 14. Further, the tube 70 covers an outer peripheral surface of a base end portion of the outer cylinder 46 including the open end 46a and the swaged portions 47a and 47b. In this embodiment, the tube 70 is a varnish tube formed by coating a surface of a braid tube formed of glass fiber with a silicon material. The material of the tube 70 is not limited thereto, and for example, the tube 70 may be formed of resin fiber, such as polyester, instead of the glass fiber. The lead wires 48 are doubly covered with their own coverings and the tube 70.

Figure 3:
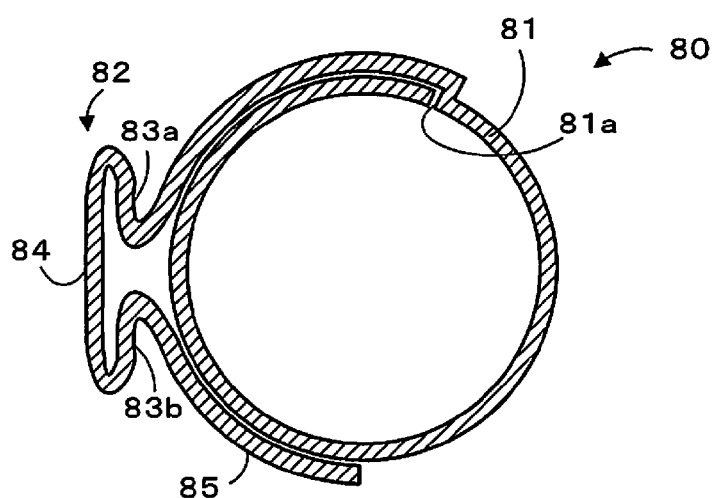
FIG. 3 is a cross-sectional view of a clamp 80.

A portion of the outer peripheral surface of the outer cylinder 46 covered with the tube 70 is gripped by a clamp 80. FIG. 3 is a cross-sectional view of the clamp 80. FIG. 3 illustrates a cross section of the clamp 80 taken along line A-A of FIG. 2. The clamp 80 is a metallic ear clamp, and includes a ring portion 81 and an ear portion 82. The ring portion 81 and the ear portion 82 are formed by bending one platelike member, and the ring portion 81 surrounds the tube 70 and the outer peripheral surface of the outer cylinder 46. An inner peripheral surface of the ring portion 81 is in contact with the tube 70. An end portion of an arc of the ring portion 81 fits in a groove 81a provided in an inner peripheral surface of the ring portion 81. Thus, the clamp 80 is structured as a so-called stepless clamp such that the inner peripheral surface of the ring portion 81 does not have a stepped portion. The ear portion 82 includes a bridge portion 84 shaped like a substantially flat plate, and leg portions 83a and 83b swaged from the upper and lower sides in FIG. 3. By swaging the leg portions 83a and 83b, the clamp 80 grips the tube 70 and the outer cylinder 46 at the ring portion 81. A curved portion 85 extending from the leg portion 83b toward the right lower side in FIG. 3 is fixed to an outer peripheral surface of the ring portion 81 by inserting a projection (not illustrated) provided on the outer peripheral surface of the ring portion 81 in a hole (not illustrated) provided in the curved portion 85.

As illustrated in FIG. 2, the clamp 80 is located to extend over the outer peripheral surfaces of the swaged portions 47a and 47b. Also, the tube 70 extends toward the free end side (left direction in FIG. 2) farther than the clamp 80. That is, the tube 70 protrudes from the clamp 80 to the side opposite from the open end 46a. While a protrusion amount L of the clamp 80 is not particularly limited as long as it is more than 0 mm, for example, the protrusion amount L is 0.5 to 1.0 mm. Further, an outer diameter D2 of the open end 46a is larger than an inner diameter D1 of the clamp 80. That is, the open end 46a is a large-diameter portion whose outer diameter is larger than the inner diameter D1. The maximum diameter D3 of the rubber plug 60 and the maximum diameter D4 of the tube 70 are both larger than the inner diameter D1, and D1<D2<D3<D4. The maximum diameter D3 is the outer diameter of a portion having the largest diameter in the part of the rubber plug 60 closer to the open end 46a than the clamp 80 (the maximum diameter of the protruding portion 60b in the embodiment). Similarly, the maximum diameter D4 is the outer diameter of a portion having the largest diameter in the part of the tube 70 between the clamp 80 and the base end of the sensor body 12 (in the embodiment, the base end of the rubber plug 60 (right end of the rubber plug 60 in FIG. 2)). That is, in the embodiment, the maximum diameter D4=the maximum diameter D3+the thickness of the tube 70×2.

The external connecting part 14 includes a plurality of terminal electrodes connected to the lead wires 48 via unillustrated crimp terminals. This allows the terminal electrodes of the external connecting part 14 to have continuity to the electrodes of the sensor element 20 via the lead wires 48. For example, when the external connecting part 14 is connected to a control unit of the vehicle, the control unit can apply voltage to the sensor element 20 via the terminal electrodes of the external connecting part 14 and can take out signals (electromotive force or current).

Next, a production method for the gas sensor 10 will be described. First, a main metal piece 41 and an inner cylinder 42 are coaxially assembled by welding, and the inside of the assembly is filled with a ceramic supporter 43a, ceramic powder 44a, a ceramic supporter 43b, ceramic powder 44b, a ceramic supporter 43c in this order from the side of the main metal piece 41. Then, a metal ring 45 is inserted. Next, a sensor element 20 is passed through the ceramic supporter 43c, the ceramic powder 44b, the ceramic supporter 43b, the ceramic powder 44a, and the ceramic supporter 43a in this order from the side of the metal ring 45. In the ceramic supporters 43a to 43c, the ceramic powders 44a and 44b, and the metal ring 45, holes through the sensor element 20 can penetrate are formed beforehand. Then, the metal ring 45 and the main metal piece 41 are pressed in a direction to approach each other to compress the ceramic powders 44a and 44b. In this state, a portion of the inner cylinder 42 on the outer side (upper side in FIG. 1) of the metal ring 45 is reduced in diameter by swaging, and a portion of the inner cylinder 42 where the ceramic powder 44b is disposed is reduced in diameter by swaging, so that a primary assembly formed by the main metal piece 41 and the sensor element 20 is obtained.

Figure 4:
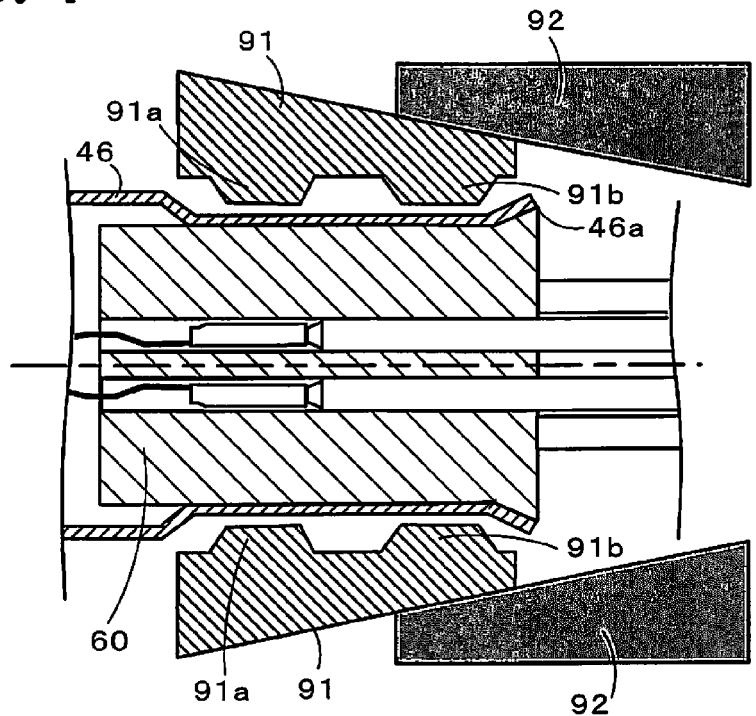
FIG. 4 is an explanatory view illustrating how an outer cylinder 46 and a rubber plug 60 are swaged.

When the primary assembly is thus obtained, an inner protective cover 31 and an outer protective cover 32 are attached to the main metal piece 41 by welding to form a protective cover 30, and an outer cylinder 46 is attached to the main metal piece 41 by welding. Subsequently, a rubber plug 60 having a through hole 60a is prepared. Then, lead wires 48 extending through the through hole 60a of the rubber plug 60 and a connector 50 in which connecting portions 52a of contact metal pieces 52 are connected to the lead wires 48 are prepared, the connector 50 is connected to a base end of the sensor element 20, and the rubber plug 60 is inserted into the outer cylinder 46 from an open end 46a. Next, the outer cylinder 46 and the rubber plug 60 are reduced in diameter by swaging to fix the rubber plug 60 to the outer cylinder 46. FIG. 4 is an explanatory view illustrating how the outer cylinder 46 and the rubber plug 60 are swaged in the production process of the gas sensor 10.

Figure 5:
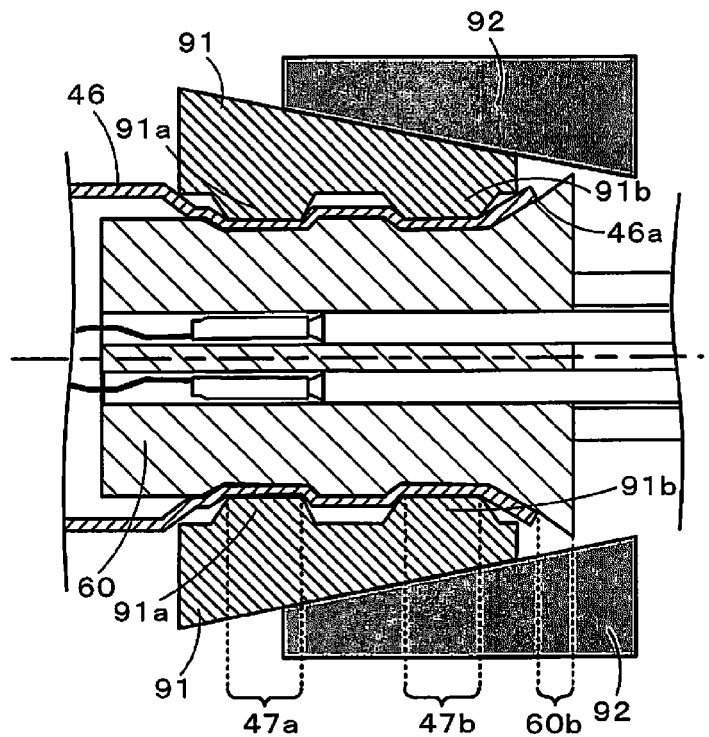
FIG. 5 is an explanatory view illustrating a state after the outer cylinder 46 and the rubber plug 60 are swaged.

As illustrated in FIG. 4, swaging is performed using a swaging jig 91 set in a swaging device (not illustrated) and a pressing jig 92 that presses the swaging jig 91 from the back side. The swaging jig 91 has two projections 91a and 91b to swage swaged portions 47a and 47b. The swaging jig 91 is shaped in the form obtained by dividing a cylindrical member at intervals of 45° into eight parts. For this reason, when eight swaging jigs 91 are prepared so that the projections 91a and 91b face toward the inner peripheral side and the primary assembly is set in the middle among the swaging jigs 91, the swaging jigs 91 are disposed to surround the periphery of the cylindrical outer cylinder 46. By moving the pressing jig 92 leftward in FIG. 4 in this state, the swaging jigs 91 are substantially horizontally moved from the outer peripheral side toward the center side (toward the outer cylinder 46) by being pressed by the pressing jig 92. Thus, swaging is performed with the projections 91a and 91b being in contact with the outer cylinder 46. FIG. 5 is an explanatory view illustrating a state after the outer cylinder 46 and the rubber plug 60 are swaged. By this swaging, swaged portions 47a and 47b are formed, and the inside of the outer cylinder 46 is sealed by the rubber plug 60 from the outside of the open end 46a. As illustrated in FIG. 4, an end portion of the rubber plug 60 is located at the same position as the open end 46a in the state before swaging. When swaging is performed, the rubber plug 60 is expanded in the axial direction (right-left direction in FIG. 4) by the pressing force resulting from swaging, and a part of the rubber plug 60 protrudes out from the open end 46a to form a protruding portion 60b (FIG. 5).

Figure 6:
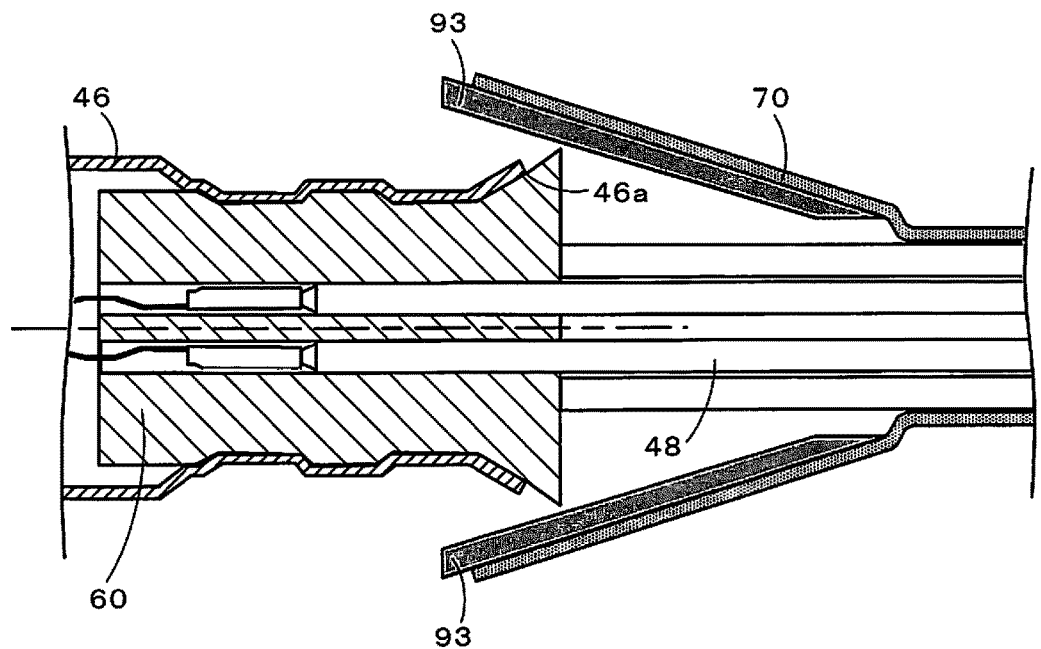
FIG. 6 is an explanatory view illustrating a covering step of covering the outer cylinder 46 with a tube 70.
Figure 7:
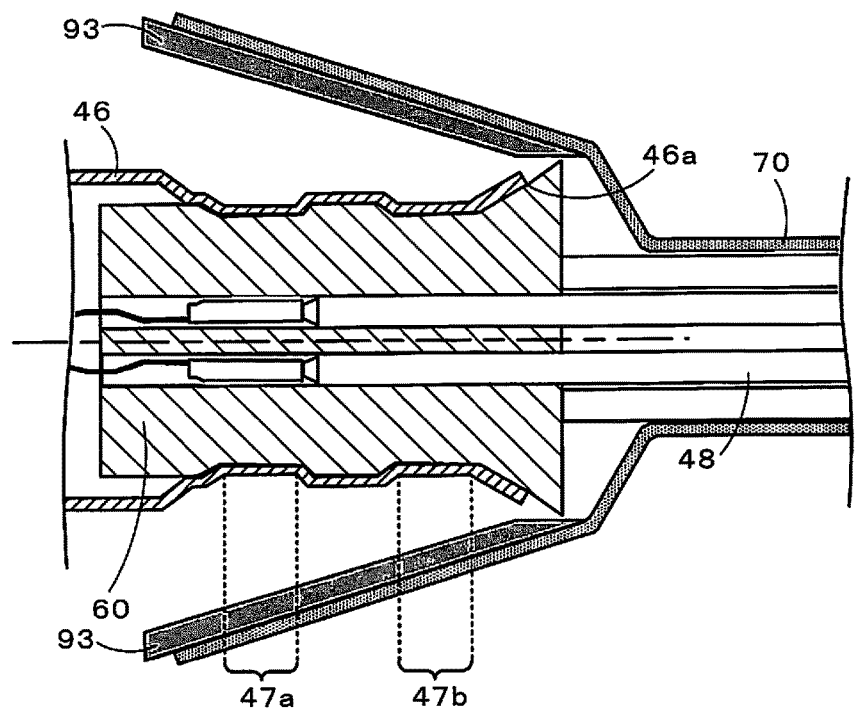
FIG. 7 is an explanatory view illustrating the covering step of covering the outer cylinder 46 with the tube 70.
Figure 8:
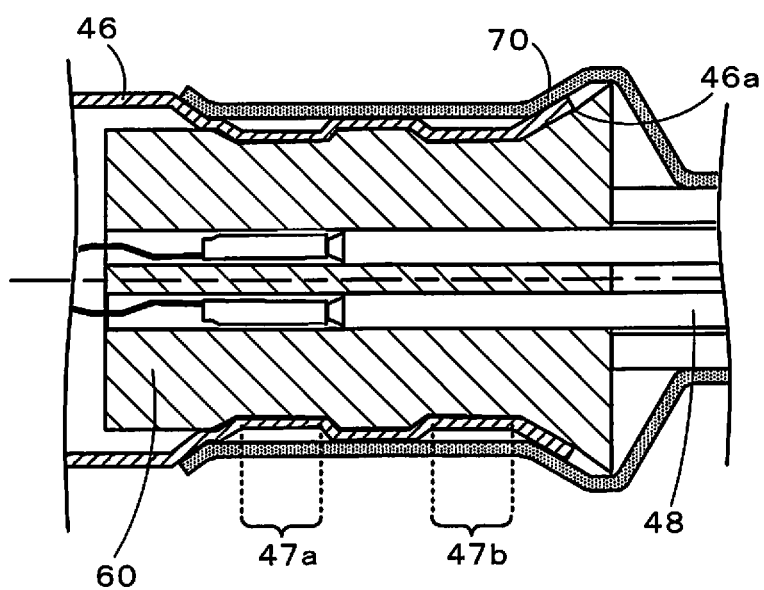
FIG. 8 is an explanatory view illustrating the covering step of covering the outer cylinder 46 with the tube 70.

Subsequently, a tube 70 is put on end portions of the lead wires 48 opposite from the outer cylinder 46 (sides to be connected to an external connecting part 14), and the tube 70 is further put on the outer cylinder 46. FIGS. 6 to 8 are explanatory views illustrating a covering step of covering the outer cylinder 46 with the tube 70. As illustrated in FIG. 6, the covering step is performed using a covering jig 93 set in a covering device (not illustrated). The covering jig 93 is shaped in the form obtained by dividing a cylindrical member having an inclined outer peripheral surface (having an outer diameter that decreases toward the right side in FIG. 6) at intervals of 180° into two upper and lower parts. In the covering step, first, as illustrated in FIG. 6, the tube 70 is put on the outer peripheral surface of the covering jig 93. Next, the outer cylinder 46 is inserted into the tube 70 while separating the upper and lower parts of the covering jig 93 to increase the diameter of the tube 70 (FIG. 7). After the outer peripheral surface of the outer cylinder 46 including the swaged portions 47a and 47b is inserted in the tube 70, the covering jig 93 is drawn out of the tube 70. Thus, the tube 70 covers the outer peripheral surface of the base end portion of the outer cylinder 46 including the open end 46a and the swaged portions 47a and 47h (FIG. 8).

Figure 9:
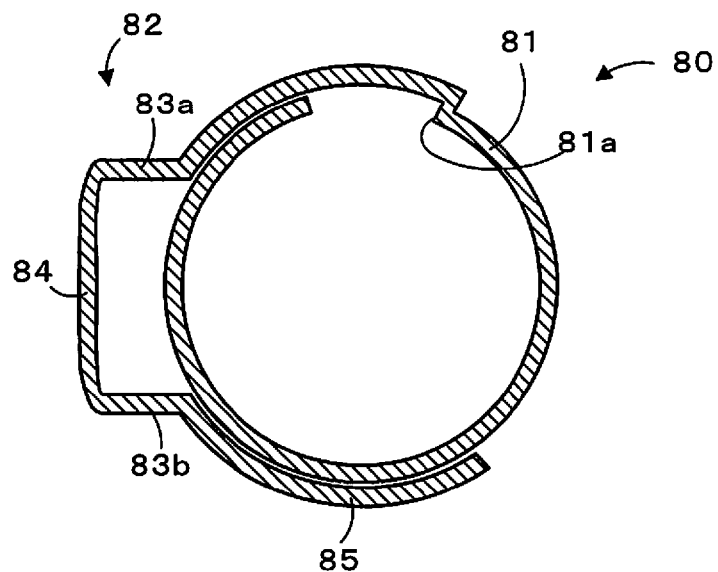
FIG. 9 is a cross-sectional view of the clamp 80 before attachment.
Figure 10:
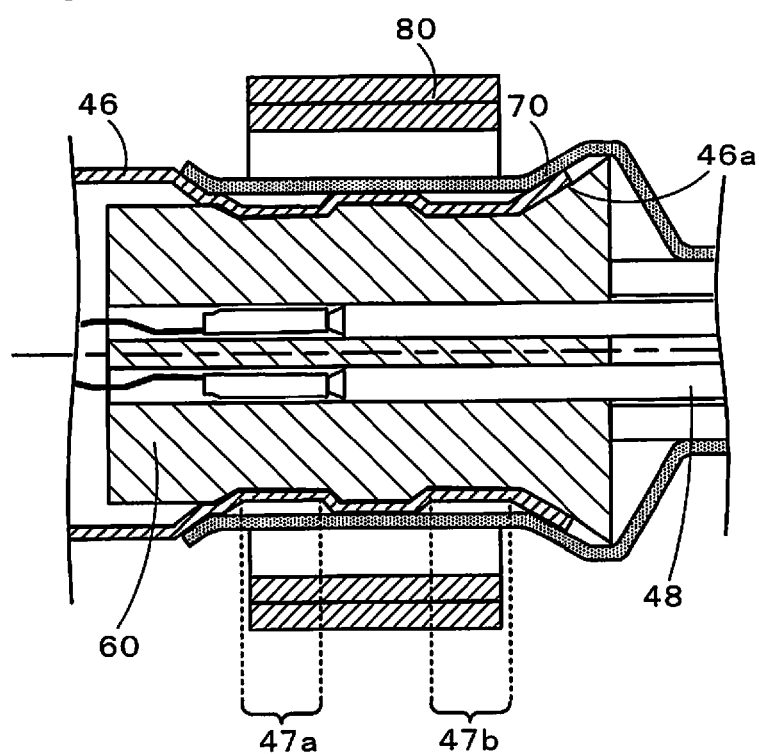
FIG. 10 is an explanatory view illustrating a state in which the clamp 80 is moved to an attachment position.

Next, a clamp 80 is attached. FIG. 9 is a cross-sectional view of the clamp 80 before attachment. Before attachment, leg portions 83a and 83b of the clamp 80 are not swaged, and the inner diameter of a ring portion 81 is larger than in FIG. 3. To attach the clamp 80, first, the clamp 80 is inserted from end portions of the lead wires 48 opposite from the outer cylinder 46, and is moved to an attachment position thereof. FIG. 10 is an explanatory view illustrating a state in which the clamp 80 is moved to the attachment position. The attachment position is located closer to the left side in FIG. 10 than the open end 46a so that the protrusion amount L of the clamp 80 described with reference to FIG. 2 is more than 0 mm. In the embodiment, the attachment position is such that the clamp 80 extends over the swaged portions 47a and 47b, as illustrated in FIG. 2. By clamping and pressing the leg portions 83a and 83b in a direction to approach each other with an unillustrated clamping tool like pliers in this state, the clamp 80 is swaged. Thus, the clamp 80 is brought into a state illustrated in FIG. 3, the ring portion 81 is reduced in inner diameter to grip the outer cylinder 46 and the tube 70, and a state illustrated in FIG. 2 is brought about. Then, the end portions of the lead wires 48 opposite from the outer cylinder 46 are connected to an external connecting part 14. Through the above steps, the gas sensor 10 illustrated in FIG. 1 is obtained.

Herein, the correspondence relationships between the constituent elements in the embodiment and the constituent elements in the present invention will be clarified. The sensor element 20 in the embodiment corresponds to the sensor element in the present invention, the open end 46a corresponds to the open end, the outer cylinder 46 corresponds to the cylindrical body, the lead wires 48 correspond to the lead wire, the tube 70 corresponds to the tube, and the clamp 80 corresponds to the grip member. Further, the open end 46a corresponds to the large-diameter portion.

Figure 11:
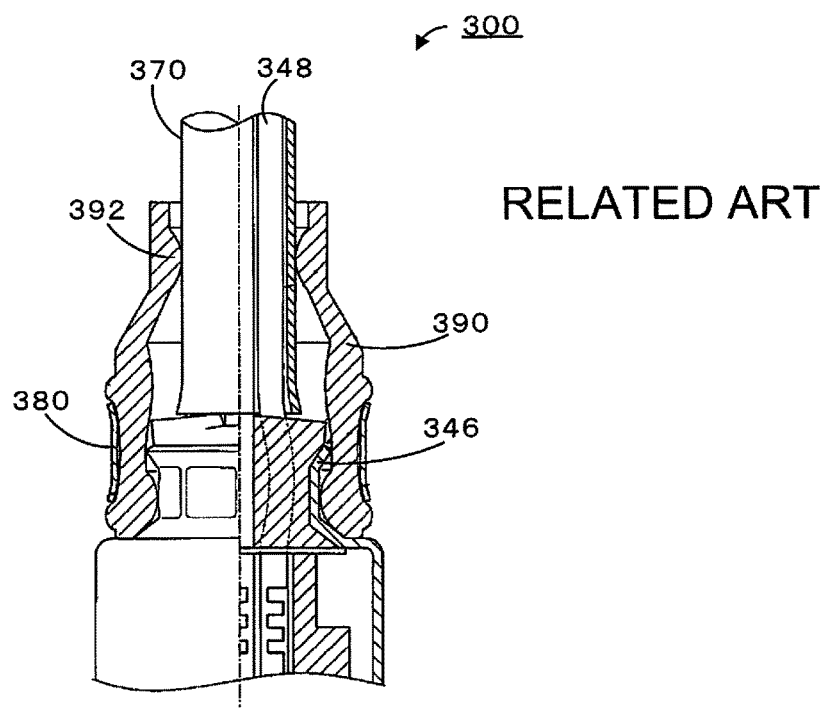
FIG. 11 is an explanatory view of an end portion of a gas sensor 300 of the related art.

In the above-described embodiment, not only the tube 70 covers the lead wires 48, but also the tube 70 covers the outer peripheral surface of the end portion of the outer cylinder 46 including the open end 46a. The portion of the outer peripheral surface of the outer cylinder 46 covered with the tube 70 is gripped by the clamp 80. Thus, the clamp 80 integrally grips the tube 70 and the outer cylinder 46. Moreover, the tube 70 protrudes from the clamp 80 to the side opposite from the open end 46a of the outer cylinder 46 (protrusion amount L>0). Thus, the tube 70 is unlikely to come out from the open end 46a of the outer cylinder 46, and the tube 70 can be fixed more reliably. For this reason, for example, exposure of the lead wires 48 and the entry of water into the sensor (into the outer cylinder 46) can be suppressed further. For example, while the clamp member 380 and the cover member 390 are used in the gas sensor 300 of the related art illustrated in FIG. 11, in the embodiment, the tube 70 and the outer cylinder 46 are gripped only by the clamp 80, and the cover member 390 is not needed. For this reason, compared with the gas sensor 300 of FIG. 11, it is possible not only to more reliably fix the tube 70 and but also to reduce the number of components and the number of man-hours in production.

The maximum diameter D4 of the tube 70 closer to the open end 46a than the portion gripped by the clamp 80 is larger than the inner diameter D1 of the clamp 80. Hence, the clamp 80 is unlikely to come out from the open end 46a of the outer cylinder 46, and the tube 70 can be fixed more reliably.

It is needless to say that the present invention is not limited to the above-described embodiment and can be carried out by various modes as long as the modes belong to the technical field of the present invention.

For example, while the inner diameter D1<the outer diameter D2 in FIG. 2 in the above-described embodiment, the relationship therebetween may be such that the inner diameter D1=the outer diameter D2 or the inner diameter D1>the outer diameter D2. This also applies to the relationships between the inner diameter D1 and the outer diameters D3 and D4. However, it is preferable that the inner diameter D1≤the maximum diameter D4, because the clamp 80 does not easily come out from the open end 46a of the outer cylinder 46.

While the outer diameter D2 of the open end 46a is larger than the inner diameter D1 of the clamp 80, that is, the open end 46a forms the large-diameter portion in the above-described embodiment, the present invention is not limited thereto. For example, another large-diameter portion may be provided between the clamp 80 and the open end 46a. For example, the clamp 80 may grip only the swaged portion 47a of the outer cylinder 46, and the outer diameter of the portion between the swaged portion 47a and the swaged portion 47b in the outer cylinder 46 may be larger than the inner diameter D1.

While the clamp 80 is the stepless clamp having the ear portion 82 in the above-described embodiment, any clamp may be used. Further, the grip member is not limited to the clamp, and any grip member may be used as long as it grips the tube 70 and the outer cylinder 46. For example, the tube 70 and the outer cylinder 46 may be gripped by a resin tying band instead of the clamp 80. While the clamp 80 and the tying band are each a ring-shaped member that surrounds the outer peripheral surface of the outer cylinder 46, for example, the grip member may have a shape, such as a C-shape or a V-shape, different from the ring shape.

While the rubber plug 60 protrudes from the open end 46a in the above-described embodiment, the present invention is not limited thereto. For example, the end portion of the rubber plug 60 may be located at the same position as the open end 46a, or the end portion of the rubber plug 60 may be located closer to the sensor element 20 (left side in FIG. 2) than the open end 46a. When the rubber plug 60 is located closer to the sensor element 20 than the open end 46a, the maximum diameter D4 of the tube 70 is the outer diameter of the portion of the tube 70 having the largest diameter in the part between the clamp 80 and the open end 46a. In this case, the maximum diameter D4=[the outer diameter of the portion of the outer cylinder 46 having the largest diameter in the part between the clamp 80 and the open end 46a]+the thickness of the tube 70×2.

While the clamp 80 grips the tube 70 and the outer cylinder 46 at the position such as to extend over the swaged portions 47a and 47b in the above-described embodiment, the present invention is not limited thereto. For example, the clamp 80 may grip the tube 70 and the outer cylinder 46 only at one of the swaged portions 47a and 47b. Alternatively, the clamp 80 may grip the tube 70 and the outer cylinder 46 at a position different from the swaged portions 47a and 47b.

While the outer cylinder 46 has the swaged portions 47a and 47b in the above-described embodiment, the present invention is not limited thereto. For example, the outer cylinder 46 may have only any one of the swaged portions 47a and 47b.

EXAMPLES

Example 1

As Example 1, the gas sensor 10 illustrated in FIGS. 1 and 2 was produced by the above-described production method. The lead wires 48 were not connected to the external connecting part 14. The material of the outer cylinder 46 was SUS 304, and a varnish tube formed by applying a silicon material onto an outer peripheral surface of a glass fiber braid sleeve and curing the silicon material at 200° C. was used as the tube 70. As the clamp 80, a stepless ear clamp 14.8-706RD from Oetiker was used. The axial length of the swaged portion 47a was 2.5 mm, the axial length of the swaged portion 47b was 2.5 mm, and the axial distance between the swaged portion 47a and the swaged portion 47b was 3.5 mm. The outer peripheral surface of a portion of the outer cylinder 46 extending by 10 mm in the axial direction from the open end 46a, including the swaged portions 47a and 47b, was covered with the tube 70. The clamp 80 was attached at a position such that the protrusion amount L was 0.5 mm, and gripped the tube 70 and the outer cylinder 46. The inner diameter D1 of the clamp 80 was 12.3 mm, the band width (axial length) of the clamp 80 was 7 mm, the outer diameter D2 of the open end 46a was 11.8 mm, the maximum diameter D3 of the rubber plug 60 was 12.0 mm, the maximum diameter D4 of the tube 70 was 12.8 mm, and the inner diameter of the tube 70 (diameter of the portion covering the lead wires 48 on the outer side of the open end 46a) was 8.5 mm.

Comparative Example 1

As Comparative Example 1, a gas sensor that was similar to Example 1 except that the clamp 80 was not attached was produced.

Measurement of Tensile Strength

In the gas sensors of Example 1 and Comparative Example 1, tension was applied to the tube 70 to pull the tube 70 in the axial direction (rightward in FIG. 2). The tension applied to the tube 70 when the tube 70 completely came out from the outer cylinder 46 was measured as a tensile strength. In Example 1, the tensile strength was 20 N. In contrast, when the tensile strength was measured in five examples according to Comparative Example 1, it was 8.6 N, 7.3 N, 7.8 N, 6.4 N, and 6.6 N. This shows that the tube 70 can be more reliably fixed by covering the outer peripheral surface of the end portion of the outer cylinder 46 including the open end 46a with the tube 70 and gripping the tube 70 and the outer cylinder 46 by the clamp 80 so that the protrusion amount L>0 mm.

The present invention is not limited to the above-described examples.

The present application claims priority from Japanese Patent Application No. 2014-048307 filed on Mar. 12, 2014, the entire contents of which are incorporated herein by reference.

What is claimed is:

1. A gas sensor comprising:
    a sensor element;
    a cylindrical body in which the sensor element is disposed, the cylindrical body having an open end;
    a lead wire having electrical continuity to the sensor element and extending outward from an inside of the cylindrical body through the open end;
    a tube that covers an outer peripheral surface of an end portion of the cylindrical body including the open end and a portion of the lead wire extending outward from the open end; and
    a grip member that grips a portion of the outer peripheral surface of the cylindrical body covered with the tube such that the tube extends beyond the grip member in an axial direction toward a side opposite from the open end,
    a maximum value of an outer diameter of a portion of the tube closer to the open end than the portion gripped by the grip member being greater than or equal to an inner diameter of the grip member,
    a portion of the cylindrical body covered with the tube passing through the grip member such that the portion of the cylindrical body covered with the tube extends beyond the open end and the side opposite the open end of the grip member, and
    the tube being a flexible insulating cylindrical member.

2. The gas sensor according to claim 1, wherein the grip member is a ring-shaped member that surrounds the outer peripheral surface of the cylindrical body.

3. The gas sensor according to claim 1, wherein the tube protrudes to the side opposite from the open end in an axial direction by a protrusion amount L of 0.5 to 1.0 mm.

4. The gas sensor according to claim 1, further comprising:
    an elastic body through which the lead wire penetrates, the elastic body being disposed within the cylindrical body to seal inside of the cylindrical body from an outside of the open end,
    wherein the cylindrical body has a diameter-reduced portion that swages the elastic body from a periphery.

5. The gas sensor according to claim 1, wherein the cylindrical body has one or more swaged portions and the grip member extends over an outer peripheral surface of at least one of the swaged portions.

6. The gas sensor according to claim 1, wherein the grip member is a stepless clamp having an ear portion.

7. The gas sensor according to claim 1, wherein the tube covers an entire portion of the lead wire between the end portion of the cylindrical body and an external connecting part.

8. The gas sensor according to claim 1, wherein the tube is formed of a material selected from the group consisting of: a glass fiber and a polyester resin.

* * * * *